(12) United States Patent
Park

(10) Patent No.: US 8,444,600 B2
(45) Date of Patent: *May 21, 2013

(54) REPLACEABLE HEATING CARTRIDGE FOR USE WITH A WARMING DEVICE FOR MEDICAL TREATMENT

(76) Inventor: Jae Sang Park, Seoul (KR)

(*) Notice: Subject to any disclaimer, the term of this patent is extended or adjusted under 35 U.S.C. 154(b) by 441 days.

This patent is subject to a terminal disclaimer.

(21) Appl. No.: 12/781,298

(22) Filed: May 17, 2010

(65) Prior Publication Data
US 2010/0222740 A1 Sep. 2, 2010

Related U.S. Application Data

(63) Continuation-in-part of application No. 10/572,118, filed as application No. PCT/KR2004/002386 on Sep. 17, 2004, now Pat. No. 7,731,688, application No. 12/781,298, which is a continuation-in-part of application No. PCT/KR2009/004078, filed on Jul. 22, 2009.

(30) Foreign Application Priority Data

Sep. 17, 2003 (KR) .................. 10-2003-0064398
Jul. 22, 2008 (KR) .................. 10-2008-0071344

(51) Int. Cl.
*A61F 7/12* (2006.01)
(52) U.S. Cl.
USPC .......................................... 604/113; 604/291
(58) Field of Classification Search
USPC .......................................... 604/113, 114, 291
See application file for complete search history.

(56) References Cited

U.S. PATENT DOCUMENTS

| 953,042 A | 3/1910 | Lamb |
|---|---|---|
| 1,110,919 A | 9/1914 | Gamble |

(Continued)

FOREIGN PATENT DOCUMENTS

| JP | 2004-105599 A | 4/2004 |
|---|---|---|
| KR | 10-0350576 | 8/2002 |

(Continued)

OTHER PUBLICATIONS

Sung Won Jung et al., Performance Characteristics of High Efficiency Fluid and Blood Warmer using Print Circuit Board Heater at Various Flow Rates, the Journal of the Korean Society of Anesthesiologists, vol. 51, No. 5, Nov. 2006, pp. 598-605.

*Primary Examiner* — Kevin C Sirmons
*Assistant Examiner* — Deanna K Hall
(74) *Attorney, Agent, or Firm* — IM IP Law PLLC; C. Andrew Im

(57) ABSTRACT

A replaceable heating cartridge for use with a warming device to heat or warm a fluid. The replaceable heating cartridge comprises a heater having first and second sides, a first connecting portion to receive a fluid from an external source, a second connecting portion to supply a heated fluid, a plurality of barrier members disposed on each side of the heater, and a pair of cover members. Each cover member is disposed on one side of the heater and configured to couple to each other with the heater and the barrier members therein between to form a body with a fluid path. The fluid path wraps around the heater multiple times to warm the fluid flowing through the fluid path from the first connecting portion to supply the heated fluid at the second connecting portion. An air filter is disposed on the fluid path to remove air from the fluid. Preferably, one of the cover member further comprises a plurality of openings to discharge the air removed from the fluid by the air filter.

22 Claims, 8 Drawing Sheets

U.S. PATENT DOCUMENTS

| | | |
|---|---|---|
| 4,427,009 A | 1/1984 | Wells et al. |
| 4,847,470 A | 7/1989 | Bakke |
| 5,269,749 A | 12/1993 | Koturov |
| 5,420,962 A | 5/1995 | Bakke |
| 5,571,153 A | 11/1996 | Wallsten |
| 6,236,809 B1 | 5/2001 | Cassidy et al. |
| 7,236,694 B1 | 6/2007 | Chammas |
| 7,731,688 B2 * | 6/2010 | Park .............................. 604/113 |

FOREIGN PATENT DOCUMENTS

| | | |
|---|---|---|
| KR | 10-0553129 A | 3/2005 |
| KR | 1020050028111 A | 3/2005 |

* cited by examiner

REPLACEABLE HEATING CARTRIDGE FOR USE WITH A WARMING DEVICE FOR MEDICAL TREATMENT

RELATED APPLICATIONS

This application is a continuation-in-part of U.S. application Ser. No. 10/572,118 filed Mar. 16, 2006, now U.S. Pat. No. 7,731,688, which is §371 application of PCT/KR04/02386 filed Sep. 17, 2004, which claims priority from Korean Patent Application No. 10-2003-0064398 filed Sep. 17, 2003, each of which is incorporated herein by reference in its entirety. This application is a continuation-in-part of PCT/KR2009/004078 filed Jul. 22, 2009, which claims priority to Korean Patent Application No. 10-2008-0071344 filed Jul. 22, 2008, each of which is incorporated herein by reference in its entirety.

TECHNICAL FIELD

The present invention relates to a warming device for a medical treatment, particularly to a replaceable heating cartridge for using with the warming device.

BACKGROUND OF THE INVENTION

Conventionally, when injecting a liquid or blood to human body, a device required for injecting the liquid or blood by getting the liquid or blood to be warm up at similar temperature to a body temperature.

The liquid or blood is maintained at a lower temperature in order to prevent them from rotten or prevent an occurrence of harmful materials therein. In the event that the liquid or blood was injected to the human body, an energy for the patient's metabolism is required to maintain the temperature of the injected liquid or blood equal to that of the patient's body. Further, in the event that the liquid or blood of lower temperature is injected to the patient, it may drop the temperature of the patient's body and cause the patient to have a heart attack, even death. In particular, in case of a patient under a general anesthetic where the patent's temperature cannot be controlled, it makes the patent feel the cold severely after the operation and stimulates a cooling point in the tissue to which the liquid and blood is injected to thereby feel a cooling pain.

Accordingly, prior to injecting a liquid or blood to the patient's body, it is necessary to warm the liquid or blood at similar temperature to the patient's body temperature.

Also, in the event that the liquid or blood is getting warm up, a gas may be generated. If the generated gas is not properly removed, it may block the smooth circulation of the blood, and particularly when a capillary is blocked, it may cause a necrosis of cell resulting in occurrence of side effects such as aeroembolism.

Therefore, the claimed invention proceeds upon the desirability of providing a sanitary replaceable heating cartridge that discharges generated gas for use with a warming device for medical treatment.

SUMMARY OF THE INVENTION

In accordance with an exemplary embodiment of the claimed invention provides a replaceable heating cartridge for use with a warming device for medical treatment.

In accordance with an exemplary embodiment of the claimed invention, the replaceable heating cartridge as aforesaid is capable of effectively warming a liquid or blood.

In accordance with an exemplary embodiment of the claimed invention, the replaceable heating cartridge as aforesaid is capable of effectively removing air generated in a liquid or blood. In accordance with an exemplary embodiment of the claimed invention, the replaceable heating cartridge for warming fluid comprises a heater having first and second sides, a first connecting portion to receive a fluid from an external source, a second connecting portion to supply a heated fluid, a plurality of barrier members disposed on each side of the heater, a pair of cover members, and an air filter. Each cover member is disposed on one side of the heater. The cover members are configured to couple to each other with the heater and the barrier members therein between to form a body with a fluid path wrapping around the heater multiple times to warm said fluid flowing through the fluid path from the first connecting portion to supply the heated fluid at the second connecting portion. The air filter is disposed on the fluid path to remove air from the fluid.

In accordance with an exemplary embodiment of the claimed invention, the heater is a printed circuit board type (PCB-type) heater formed on an insulating substrate comprising resistive patterns formed on both surfaces of the insulating substrate.

In accordance with an exemplary embodiment of the claimed invention, the barrier members are formed on an internal surface of each cover member. In accordance with an aspect of the claimed invention, each cover member and associated barrier members are formed by integral injection molding.

In accordance with an exemplary embodiment of the claimed invention, the barrier members on a first cover member are sloped in a first direction and the barrier members on a second cover member are sloped in a second direction to form the fluid path in a shape of a screw thread.

In accordance with an exemplary embodiment of the claimed invention, the air filter is disposed on an internal surface of one of the cover members.

Various other objects, advantages and features of the present invention will become readily apparent from the ensuing detailed description, and the novel features will be particularly pointed out in the appended claims.

BRIEF DESCRIPTION OF THE DRAWINGS

The following detailed description, given by way of example, and not intended to limit the present invention solely thereto, will best be understood in conjunction with the accompanying drawings in which.

DETAILED DESCRIPTION OF THE EMBODIMENTS

Figure 1:
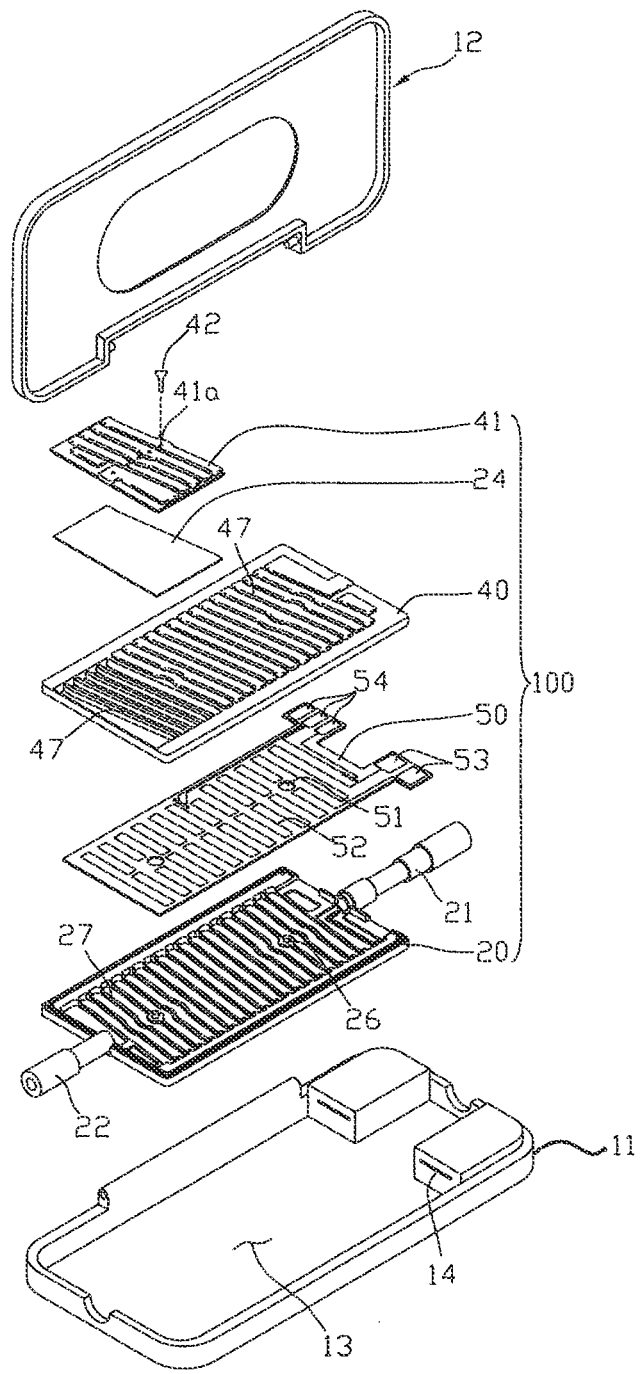
FIG. 1 is a perspective view of a replaceable heating cartridge for use with a warming device for medical treatment in accordance with an exemplary embodiment of the claimed invention.

In describing embodiments according to the present invention, in the event that each layer (film) area, pattern or structure are described to be formed "on" or "under" a substrate, each layer (film), area, pad or patterns, the terms "on" and "under" is intended to cover the meaning of "directly "on" and "under" or "indirectly "on" and "under" through other layer. Also, the criterion of on/under each layer is described on the basis of the drawings.

In the drawings, the thickness or size of each layer is illustrated exaggeratedly, abbreviately or schematically for the convenience and clearness of the explanation. Also, the size of each constituent element does not fully reflect its actual size.

Now, a replaceable heating cartridge for use with a warming device for medical treatment in accordance with exemplary embodiments of the claimed invention will be described in detail with reference to the accompanying drawings.

Figure 2:
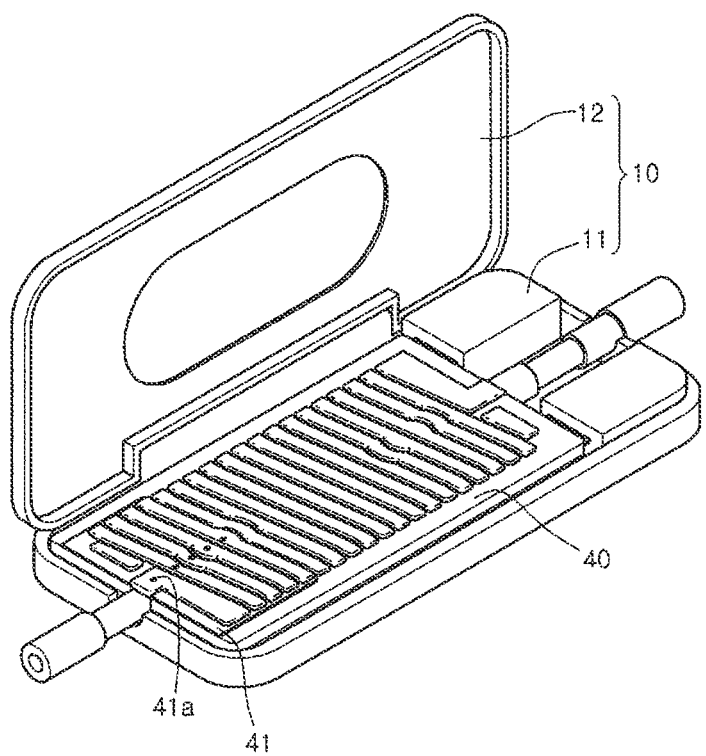
FIG. 2 is a view showing the assembled state of the replaceable heating cartridge in a warming device for medical treatment in accordance with an exemplary embodiment of the claimed invention.

FIG. 1 is a perspective view of a replaceable heating cartridge for use with a warming device for medical treatment in accordance with an exemplary embodiment of the claimed invention, and FIG. 2 is a view showing an assembly of the replaceable heating cartridge in a warming device for medical treatment in accordance with an exemplary embodiment of the claimed invention.

Referring to FIGS. 1 and 2, the warming device for medical treatment in accordance with an exemplary embodiment of the claimed invention is provided with a case or housing in which a lower case (11) and a upper case (12) are coupled each other. A replaceable heating cartridge (100) is disposed on a mounting portion of the housing between the lower case (11) and the upper case (12). After use, the operator can removed the used replaceable heating cartridge (100) with a new replaceable heating cartridge (100), thereby promoting safe and sanitary use of the warming device.

The replaceable heating cartridge (100) provides a warming function for warming such fluid as blood and liquid and an air filtering function for removing an air in the fluid. In accordance with an exemplary embodiment of the claimed invention, the replaceable heating cartridge (100) comprises a first cover member (20), a heater (50), a second cover member (40), a filter (24) and an optional third cover member (41).

The first cover member (20) and the second cover member (40) are coupled to each other with the heater (50) and filter (24) sandwiched there between to form a body of the replaceable heating cartridge (100). Alternatively, the replaceable heating cartridge can comprise an optional third cover member (41) coupled to the third cover member (40) with the filter (24) sandwiched there between.

In accordance with an exemplary embodiment of the claimed invention, a plurality of first barrier members (27) are formed on a side opposite to the heater (50) of the first cover member (20) and a plurality of second barrier members (47) are formed on a side opposite to the heater (50) of the second cover member (20). The first cover member (20) and the first barrier member (27) can be formed by the integral injection molding, and similarly the second cover member (40) and the second barrier member (47) can be formed by means of the integral injection molding.

In accordance with an exemplary embodiment of the claimed invention, the second cover member (40) is provided with the second barrier members (47) so that the second barrier members (47) can form a fluid path together with the first barrier members (27) of the first cover member (20) corresponding thereto in which a partial area of the second cover member (40) is provided with both the second barrier members (47) and the filter (24) in a upper direction. That is, the filter (24) is disposed towards the second connecting portion (22) of the replaceable heating cartridge (100).

In accordance with an aspect of the claimed invention, the second cover member (40) is provided with the second barrier members (47) so that the second barrier members (47) can form a fluid path together with the first barrier members (27) of the first cover member (20) corresponding thereto in which a partial area of the second cover member (40) is provided with only the second barrier members (47) without being provided with a partial area of the second cover member supporting the second barrier members (47) in a upper direction. The second barrier members (47) are, at both ends thereof, supported by the second cover member (40).

In accordance with an exemplary embodiment of the claimed invention, the filter (24) is disposed on a portion of the second cover member (40) or on the optional third cover member (41) covering a partially removed portion of the second cover member (40) to remove air from the fluid flowing in the fluid path. A portion of the second cover member (40) or the optional third cover member (41) is provided with a plurality of voids or openings (41a) for outwardly discharging air removed from the fluid in the fluid path partitioned by the second barrier members (47). Preferably, each opening (41a) comprises a check valve (42) to discharge air removed from the fluid in the fluid path by the filter (24) and to prevent entry of air into the fluid from outside of the body of the replaceable heating cartridge (100). That is, the check valve (42) releases the air from the replaceable heating cartridge (100) to outside but prevents air from entering the replaceable heating cartridge (100) from outside.

The first barrier members (27) are formed to be sloped in a first direction and the second barrier members (47) are formed to be sloped in a second direction to thereby form a fluid path together with the heater (50). That is, the fluid path wraps around the heater (50) multiple times, preferably in the shape of a screw thread.

The fluid path formed of a first cover member (20) comprising the first barrier members (27), a second cover member (40) comprising the second barrier members (47), optional third cover member (41) and a heater (50) is configured to surround or wrap around the heater (50) in the form of screw thread so that a heat generated from the heater (50) can be sufficiently delivered to the fluid flowing through the fluid path.

Because the width of the heater (50) is narrower than that of the formed first and second barrier members (27, 47), a front fluid path (40a) and a rear fluid path (20a) which are partitioned by the heater (50) are connected to each other at both sides of the heater (50).

In accordance with an exemplary embodiment of the claimed invention, the first cover member (20) comprises a first connection portion (21) into which a fluid flows (i.e., unheated fluid) into the replaceable heating cartridge (100) and a second connection portion (22) from which a heated fluid is discharged from the replaceable heating cartridge (100). In operation, the first cover member (20), the first barrier members (27), the heater (50), the second cover member (40), the second barrier members (47) are coupled together with or without an optional third cover member (41) to form a body of the replaceable heating cartridge (100), such that the unheated fluid inflows into the first connection portion (21) and the heated fluid is discharged through the second connection portion (22) via the fluid path formed of the first cover member (20), the first barrier members (27), the second cover member (40), the second barrier members (47), the heater (50), and optional third cover member (41). In accordance with an aspect of the claimed invention, the first and second barrier members (27, 47) are respectively formed on the internal surfaces of the first and second cover members (20, 40). The internal surfaces of the first and second cover members (20, 40) face the respective sides of the heater (50).

The first connection portion (21) is disposed at one end of the replaceable heating cartridge (100) and the second connection portion (22) is disposed at the other end of the replaceable heating cartridge (100). The unheated fluid flows into the replaceable heating cartridge (100) from an external source through the first connection portion (21), the fluid is heated while flowing in the fluid path wrapped multiple times around the heater (50), and discharges or leaves the replaceable heating cartridge (100) through the second connection portion (22). That is, the fluid is heated while flowing in the fluid path from the first connection portion (21) to the second connection portion (22).

In accordance with an exemplary embodiment of the claimed invention, the fluid inflowing through the first connection portion (21) flows through a rear fluid path (20a) formed by the rear side of the heater (50), the first cover member (20) and the first barrier members (27) in a first sloped direction (that is, a right downward direction) of the first barrier members (27) and through a front fluid path (40a) formed, at the end of the rear side fluid path, by the front side of the heater (50), the second cover member (40) and the second barrier members (47) in a second sloped direction (that is, left downward direction) of the second barrier members (47). The fluid flows through the rear fluid path (20a) formed, at a portion adjacent to the second connection portion (21), by the rear side of the heater (50), the first cover (20) and the first barrier members (27) and flows through the front fluid path (40a) formed, at the end of the rear fluid path (20a), by the front side of the heater (50), the second barrier members (47) and the second cover member (40) or the optional third cover member (41) to the second connection portion (21).

As exemplary shown in FIG. 1, in accordance with an embodiment of the claimed invention, the filter (24) is disposed adjacent to the second connection portion (22) rather than the first connection portion (21) because the fluid at higher temperature includes more air or bubbles than at a low temperature. Hence, it is more effective to dispose the filter (24) adjacent to the second connection portion (22) where the heated or warmer fluid resides in the replaceable heating cartridge (100) to provide the air filtering effects.

In accordance with an exemplary embodiment of the claimed invention, the fluid path formed by the first cover member (20), the first barrier members (27), the heater (50), the second cover member (40), the second barrier members (47) and an optional third cover member (41) is configured to surround or wrap around the filter (24) in the shape of a screw thread. The fluid inflowing through the first connection portion (21) can be sufficiently warmed by the heater (50) as the fluid traverses the fluid path from the first connection portion (21) to the second connection portion (22). Since the pressure of the fluid flowing through the fluid path is higher than outside the replaceable heating cartridge (100), the air in the fluid can be discharged to the outside of the fluid path and the replaceable heating cartridge (100) through the filter (24) and the openings (41a). Thus, in the claimed replaceable heating cartridge (100), the air is removed from the fluid through the filter (24) and the openings (41a) and the heated fluid is discharged to the outside through the second connection portion (22).

Figure 8:
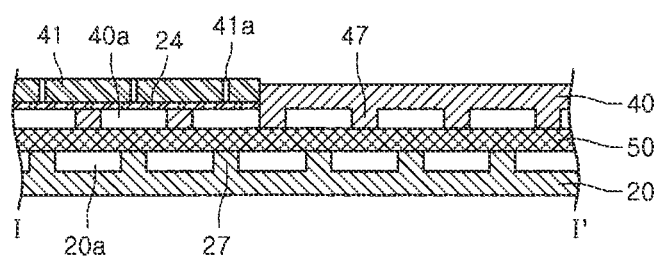
FIG. 8 is a cross-sectional view of a first cover member, a heater, a second cover member and a third cover member are coupled together in the replaceable heating cartridge in accordance with an exemplary embodiment of the invention.
Figure 9:
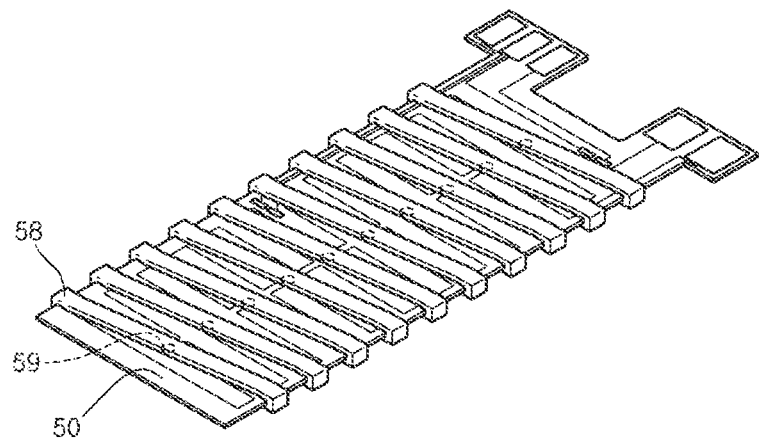
FIGS. 9-12 are views of a replaceable heating cartridge in accordance with an exemplary embodiment of the claimed invention.

In accordance with an exemplary embodiment of the claimed invention, the filter (24) is disposed at the upper side of the front fluid path (40a) horizontally with the flowing of the fluid, as exemplary shown in FIGS. 1 and 8. In accordance with an aspect of the claimed invention, the filter (24) is formed of a hydrophobic non-woven fabric having less affinity with the fluid and having fine voids formed therein. The fine void is sufficiently small in size to prevent the fluid from passing through it. The filter (24) can be attached to the second cover member (40) or the optional third cover member (41) using an ultrasonic wave or an adhesive. A portion of second cover member (40) adjacent to the filter (24) or the optional third cover member (41) is formed with a plurality of voids or openings (41a) to allow an air collected by the filter (24) to be discharged to the outside of the replaceable heating cartridge (100). Although not shown, it is appreciated that the plurality of voids (41a), the filter (24) and the optional third cover member (41) which function as an air filter may be formed on the front fluid path (40a) as well as the rear fluid path (20a).

In the replaceable heating cartridge (100) in accordance with an exemplary embodiment of the claimed invention, the filter (24) is disposed at the position opposite to the heater (50) thereby performing warming function and air filtering function at the same time. Accordingly, the claimed replaceable heating cartridge (100) can promptly remove air from the fluid warmed in the warming device (100) without using a conventional drip chamber. Additionally, the claimed replaceable heating cartridge (100) can be disposed near the patient to allow injection of the warmed fluid before the temperature of the warmed fluid drops. Further, as noted herein, it is not necessary to use the conventional drip chamber with the claimed replaceable heating cartridge (100), thereby resulting in an advantage that there is no need to make the first and second connection portions (21, 22) stand up and down vertically.

In accordance with an exemplary embodiment of the claimed invention, the first connection portion (21), the first cover member (20) and the second connection portion (22) can be formed integrally by an injection molding. Also, the second cover member (40) and the second barrier members (47) can be formed integrally by an injection molding. In accordance with an exemplary embodiment of the claimed invention, the heater (50) can be a PCB (Printed Circuit Board) substrate having resistive patterns (52) formed thereon.

Figure 3:
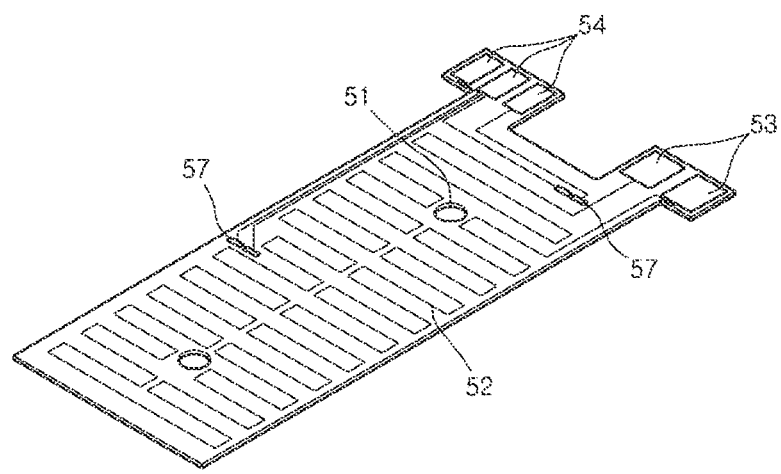
FIG. 3 is a front view of a heater in accordance with an exemplary embodiment of the claimed invention.
Figure 4:
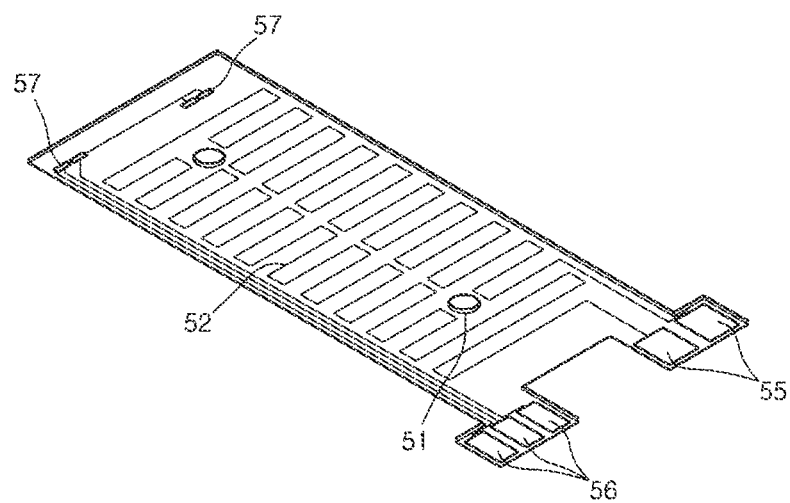
FIG. 4 is a rear view of the heater in accordance with an exemplary embodiment of the claimed invention.

Turning now to FIGS. 3-4, there are illustrated a front view of the heater (50) and a rear view of the heater (50), respectively. In accordance with an exemplary embodiment of the claimed invention, the heater (50) is a PCB substrate with resistive patterns (52) formed on the front and rear sides the PCB substrate. Heat is emitted from the resistive patterns (52) by a voltage applied through the voltage electrodes (53, 55). Also, the heater (50) has temperature sensors (57) formed at the front and rear sides thereof, and thus the temperature sensors (57) are sensing the temperature of the fluid in the fluid path and the sensed signals are sent through the temperature sensing electrodes (54, 56) to the outside, preferably to the housing of the warming device.

In accordance with an exemplary embodiment of the claimed invention, the resistive patterns (52) are formed at the front and rear sides of the PCB substrate of the heater (50). In accordance with an aspect of the claimed invention, the resistive patterns (52) on the front side of the heater (50) and the resistive patterns (52) on the rear side of the heater (50) can be electrically inter-divided, thereby simplifying the manufacturing process. That is, two voltage electrodes (53) formed on the front side of the heater (50) are applied with positive and negative voltages, respectively and similarly, the two voltage electrodes (55) formed on the rear side of the heater (50) are applied with positive and negative voltages.

In accordance with an exemplary embodiment of the claimed invention, the lower case (11) of the housing of the warming device comprises a voltage connector (14a) which connects and supplies voltage to the resistive patterns (52) through the voltage electrodes (53, 55). In accordance with an aspect of the claimed invention, the voltage connector (14a) can supply voltage to the resistive patterns (52) formed at the front and rear sides of the heater (50) in serial or parallel. It is appreciated that the resistive patterns (52) formed at the front and rear sides of the heater (50) can be electrically connected to each other. In accordance with an aspect of the claimed invention, the PCB substrate of the heater (50) can be formed with a hole or groove to which a conductive material can be buried therein. The resistive patterns (52) on the front and rear sides of the heater (50) can be electrically connected to each other via the conductive material such that positive voltage is applied to one voltage electrode (53, 55) and negative voltage is applied to another electrode (53, 55). That is, the voltage electrode (53, 55) on one side of the heater (50) acts as a positive terminal and the voltage electrode (53, 55) on the other side of the heater acts as a negative terminal. Preferably, the thickness of the conductive material buried in the PCB substrate of the heater (50) via the groove is thinner than that of the resistive patterns (52). Alternatively, the resistive patterns (52) disposed on the front side of the heater (50) and the resistive patterns (52) disposed on the rear side of the heater (50) can be made to be electrically inter-divided and positive and negative voltages are applied to each voltage electrode (53, 55).

Similar to the voltage electrodes (53, 55), the temperature sensors (57) are also formed on the front and rear sides of the heater (50) respectively and can be electrically connected to each other or divided. The temperature sensors (57) are electrically connected to the sensing electrodes (54, 56) which are formed on the front and rear sides of the heater (50) respectively.

In accordance with an exemplary embodiment of the claimed invention, as exemplary shown in FIGS. 1, 3-5, the heater (50) comprises a hole or opening (51) and the first cover member (20) comprises a protrusion (26). The protrusion (26) is insertable into the hole (51) so that the heater (50) can be disposed on an exact position on the first cover member (20).

Figure 5:
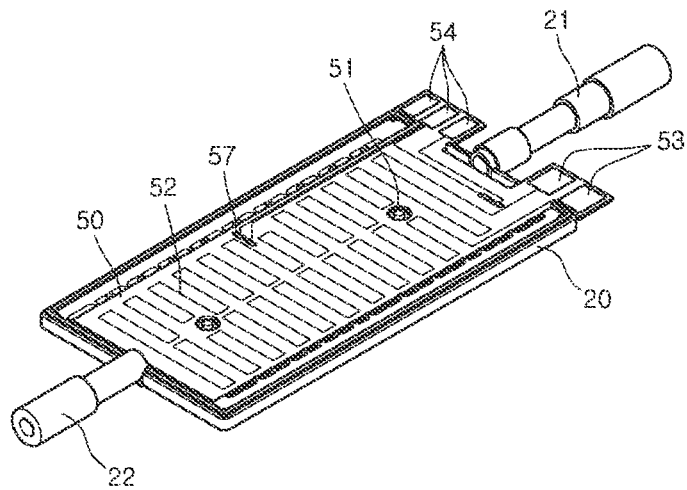
FIG. 5 is a view of a first cover member coupled to a heater in accordance with an exemplary embodiment of the claimed invention.
Figure 6:
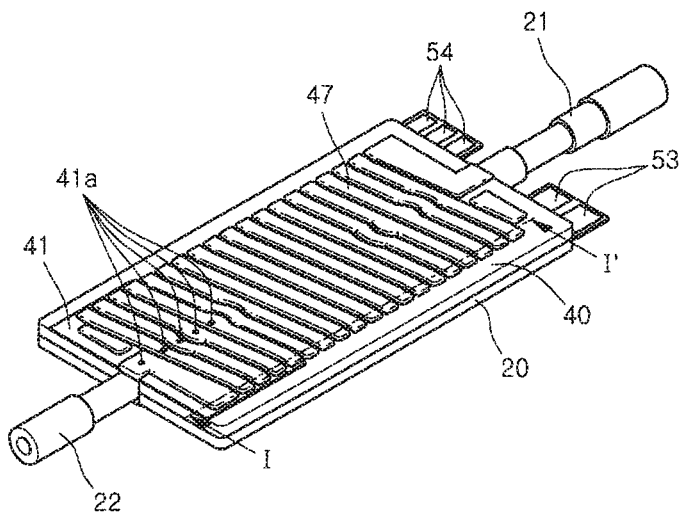
FIG. 6 is a view of a first cover member, a heater and a second cover member of the replaceable heating cartridge in accordance with an exemplary embodiment of the claimed invention.

Turning now to FIG. 5, there is illustrated a view of the heater (50) disposed on the first cover member (20) in accordance with an exemplary embodiment of the claimed invention. FIG. 6 shows a view of the first cover member (20), a heater (50) and a second cover member (40) combined or coupled to form the replaceable heating cartridge (100) with the voltage electrodes (53, 55) and the temperature sensing electrodes (54, 56) of the heater (50) protruding outwardly from the body of the replaceable heating cartridge (100) in accordance with an exemplary embodiment of the claimed invention. The voltage and temperature sensing connectors (14a, 14b) formed in the lower case (11) of the housing of the warming device are connectable to the voltage and temperature sensing electrodes (53-56) of the heater (50) in accordance with an exemplary embodiment of the claimed invention, as shown in FIG. 7.

Figure 7:
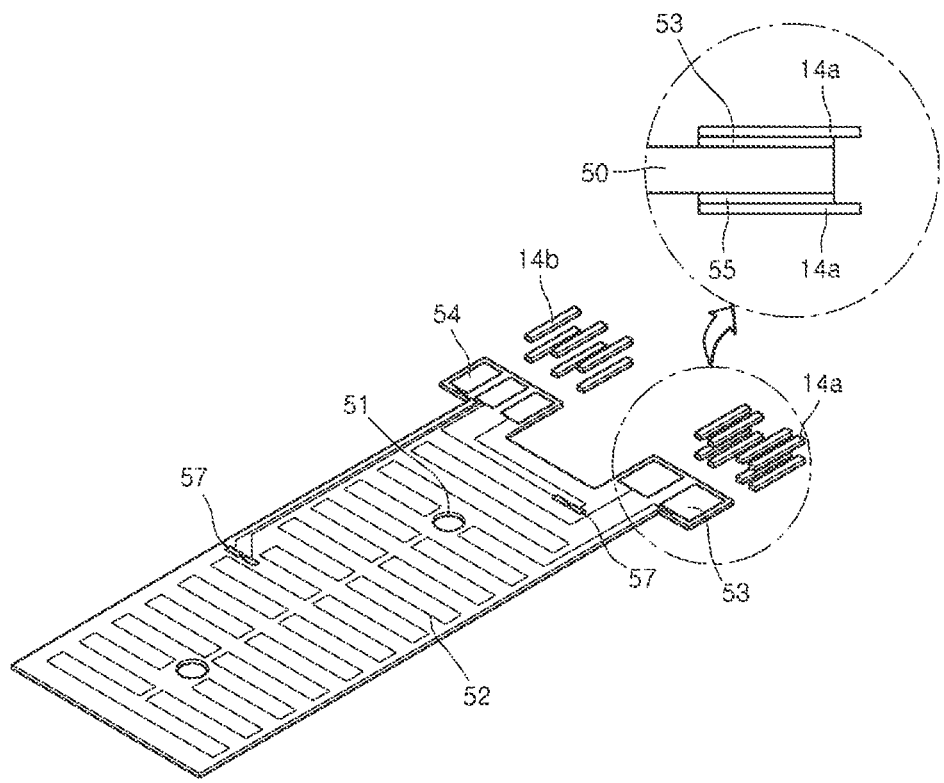
FIG. 7 is a view of voltage and temperature sensing connectors of a housing, voltage and temperature sensing electrodes of the replaceable heating cartridge in accordance with an exemplary embodiment of the claimed invention.

In accordance with an exemplary embodiment of the claimed invention, the outwardly protruding voltage electrodes (53, 55) and temperature sensing electrodes (54, 56) of the heater (50) are respectively insertable into the electrode inserting hole (14) of the lower case (11), as exemplary shown in FIG. 1, to be electrically connected with to the voltage connector (14a) and the temperature sensor connector (14b), respectively, as exemplary shown in FIGS. 2 and 7. The voltage connector (14a) and the temperature sensor connector (14b) electrically connect to the resistive patterns (52) and the temperature sensors (57) on the front and rear sides of the heater (50) via the voltage and temperature electrodes (53-56). The voltage connector (14a) supplies voltage to the resistive patterns (52) through the voltage electrodes (53, 55) from an external source. Preferably, the voltage and temperature sensor connectors (14a, 14b) are double connector structure in which the connectors (14a, 14b) are configured to electrically connect to the electrodes (53-56) on both sides of the heater (50). That is, the voltage connector (14a) and the temperature sensor connector (14b) are positioned to respectively connect to the voltage electrodes (53, 55) and the temperature sensing electrodes (54, 56) on the front and rear sides of the heater (50).

When the voltage electrodes (53, 55) and the temperature sensing electrodes (54, 56) of the replaceable heating cartridge (100) are inserted into the electrode inserting hole (14) of the lower case (11) by the operator or user, the voltage electrodes (53, 55) and the temperature sensing electrodes (54, 56) formed on the front and rear sides of the heater (50) are connected simultaneously to the voltage and the temperature sensor connectors (14a, 14b), respectively. Although not shown herein but shown in co-pending application Ser. No. 10/572,118, the lower case (11) can comprise a driving chip for driving the heater (50), a sensing signal processing portion for processing signal obtained from the temperature sensors (57), a display portion to display information to an operator or user, an input button for operating or controlling the various functions of the replaceable heating cartridge (100), such as the heating temperature and like, each of which are electrically connected to the voltage and the temperature sensor connectors (14a, 14b).

Figure 15:
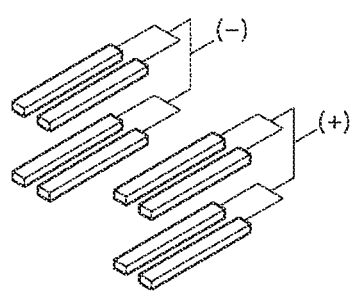
FIGS. 15-16 are views showing electrical connecting relations of voltage connectors in accordance with an exemplary embodiment of the claimed invention.
Figure 16:
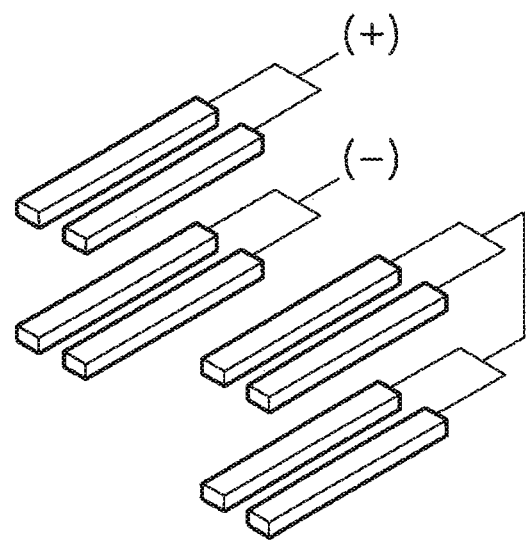

In accordance with an exemplary embodiment of the claimed invention, the various electric connection relations of the voltage connectors (14a) are exemplary shown in FIGS. 15-16. The voltage connectors (14a) are arranged in a parallel configuration to connect to the resistive patterns (52) on both sides of the heater (50) which are electrically divided from each other. That is, a positive terminal of the voltage connector (14a) is connected to resistive patterns (52) on both sides of the heater (50) and a negative terminal of the voltage connector (14a) is connected to resistive patterns (52) on both sides of the heater (50), thereby individually supplying power to the resistive patterns (52) on each side of the heater (50). Alternatively, the voltage connectors (14*a*) are arranged in a serial configuration to connect to the resistive patterns (52) on both sides of heater (50) which are electrically connected to each other. That is, a positive terminal of the voltage connector (14*a*) is electrically connected to the resistive patterns (52) on one side of the heater (50) and a negative terminal of the voltage connector (14*a*) is electrically connected to the resistive patterns (52) on the other side of the heater (50). It is appreciated that the resistance values of the resistive patterns (52) on the heater (50) will be different for the voltage connectors (14*a*) configured in a serial and parallel connection. Accordingly, when a particular heating temperature is desired, the claimed invention considers the configuration of the voltage connectors (14*a*) and the resistance values of the resistive patterns (52) on the front and rear sides of the heater (50) in determining the appropriate voltage to apply to the voltage electrode (53, 55) through the voltage connectors (14*a*) to generate the appropriate heat to heat the fluid to the desired temperature.

Turning now to FIG. 8, there is illustrated a cross-sectional view of the first cover member (20), a heater (50), a second cover member (40), and an optional third cover member (410) coupled together to form a body of the replaceable heating cartridge (100) in accordance with an exemplary embodiment of the claimed invention. The first cover member (20), the first barrier members (27) of the first cover member (20) and the rear side of the heater (50) forms the rear fluid path (20*a*), and the second cover member (40), the second barrier members (47) of the second cover member (40) and the front side of the heater (50) forms the front fluid path (40*a*). The rear fluid path (20*a*) and the front fluid path (40*a*) cross over at the center portion of the replaceable heating cartridge (100) with the heater (50) sandwiched therebetween according to the directions of the first barrier members (27) and the second barrier members (47).

It is appreciated that FIG. 8 is a cross-sectional view of the replaceable heating cartridge (100) at the position (I-I' in FIG. 6) offset one side from the center portion thereof. The first barrier members (27) and the second barrier members (47) are disposed intercross-wisely in FIG. 8. When the fluid flows through the front fluid path (40*a*) on which the filter (24) is formed, air in the fluid is removed and collected by the filter (24) and discharged outside of the replaceable heating cartridge (100) through the voids or openings (41*a*).

Figure 10:
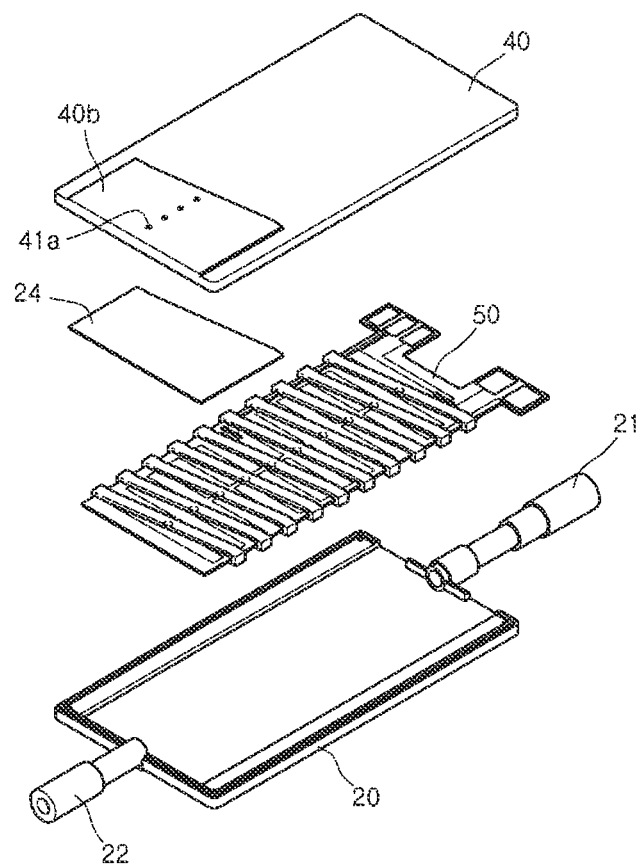
Figure 11:
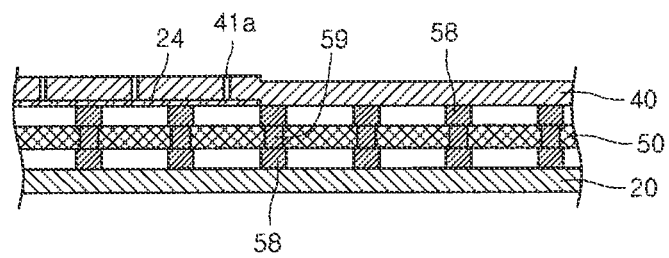
Figure 12:
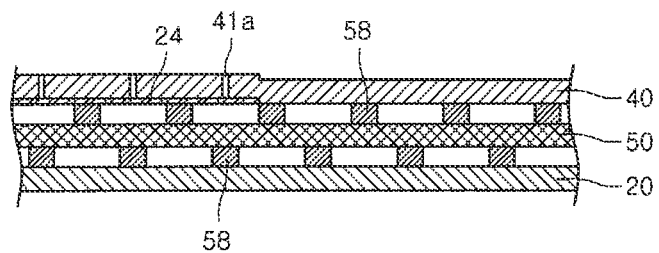

Turning now to FIGS. 9-12, there is illustrated a replaceable heating cartridge (100) in accordance with an exemplary embodiment of the claimed invention. As exemplary shown in FIG. 9, barrier members (58) are formed on both sides of the heater (50) to surround or wrap around the heater multiple times in a form of a screw thread. In accordance with an aspect of the claimed invention, the barrier members (58) can be attached to the heater (50) by an insert-injection molding together with the heater (50). FIG. 10 shows an exploded, perspective view of the replaceable heating cartridge (100) comprising the first cover member (20), a heater (50), a filter (24) and a second cover member (40) with a plurality of voids or openings (41*a*). A cross sectional view of the replaceable heating cartridge (100) of FIG. 10 is shown in FIG. 11 comprising the first cover member (20), a heater (50), a filter (24) and a second cover member (40) coupled together to form the body of the replaceable heating cartridge (100). FIG. 12 shows a cross sectional view of the replaceable heating cartridge (100) at the position offset one side from the center portion of the replaceable heating cartridge (100) such that the fluid path forms wraps around the heater (50) multiple times in a form of a screw thread.

In accordance with an exemplary embodiment of the claimed invention, the front and rear sides of the heater (50) can be applied with a coating material (not shown) so that when the barrier members (58) are insert-injected, the coating material dissolves to minimize any fine gap between the barrier members (58) and the heater (50). Preferably, the coating material is selected as a material having a melting point lower than the material forming the barrier members (58).

In accordance with an exemplary embodiment of the claimed invention, the center portion of the heater (50) comprises connection holes (59) at predetermined distance. The connection holes (59) facilitates the formation of the barrier members (58) on the front and rear sides of the heater (50), particularly the connection holes (59) insures that the barrier members (58) are coupled securely to the heater (50). When the barrier members (58) are insert-injected onto the sides of the heater (50), the material forming the barrier members (58) are also injected into the connection hole (59) to firmly secure the barrier members (58) to the sides of the heater (50). It is appreciated that the barrier members (58) are attached to the sides of the heater (50) by insert-injection molding together with the heater (50), but the barrier members (58) are not attached to either the first or second cover members (20, 40).

In accordance with an exemplary embodiment of the claimed invention, either the first or second cover member (20, 40) comprises a filter attaching portion (40*b*) to facilitate the attachment of the filter (24) thereto. FIG. 10 exemplary shows the second cover member (40) comprising the filter attaching portion (40*b*). In accordance with an aspect of the claimed invention, the filter attaching portion (40*b*) can be formed by making the thickness of the second cover member (40) thinner at the filter attaching portion (40*b*) than other portion of the second cover member (40) or making the second cover member (40) at the filter attaching portion (40*b*) protrude compared to the other portion of the second cover member (40). Also, in the same manner as described with reference to FIGS. 1 and 8, the filter attaching portion (40*b*) is provided with a plurality of voids or openings (41*a*) at positions corresponding to the fluid path to discharge air removed and collected by the filter (24).

Figure 13:
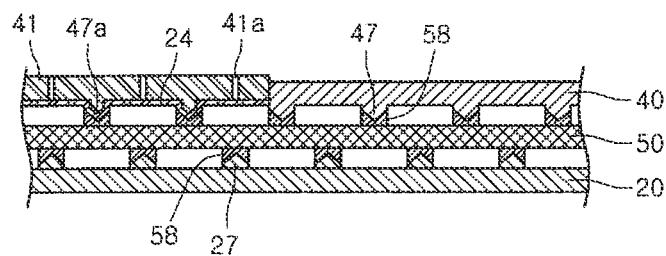
FIG. 13 is a view of a replaceable heating cartridge in accordance with an exemplary embodiment of the claimed invention.

FIG. 13 illustrates a replaceable heating cartridge (100) in accordance with an exemplary embodiment of the claimed invention. The barrier members (58) are not only formed on the front and rear sides of the heater (50), as exemplary shown in FIG. 9, but the first and second barrier members (27, 47) are also formed on the internal surfaces of the first and second cover members (20, 40), as exemplary shown in FIG. 1. As noted herein, one of the first and second cover member (20 40) comprises a plurality of voids or openings (41*a*) to discharge air removed from the fluid by the filter (24). Further, in accordance with an aspect of the claimed invention, the replaceable heating cartridge (100) can comprise an optional third cover member (41) with the third barrier member (47*a*) formed thereon. It is appreciated that the third cover member (41) can be formed integral with the second cover member (40), as exemplary shown in FIG. 11. As discussed herein, the barrier members (58) formed on the heater (50) can be coupled to the heater (50) by an insert-injection, and the first barrier members (27), the second barrier members (47) and the third barrier members (47*a*) can be formed by insert-injection together with the first cover member (20), the second cover member (40) and the third cover member (41), respectively.

As noted herein, in accordance with an aspect of the claimed invention, the filter (24) can be formed between the barrier members (58) of the heater (50) and the third cover member (41) comprising the third barrier members (47a) and a plurality of voids or openings (41a) to discharge the air removed from the fluid by the filter (24) as discussed herein.

In accordance with an exemplary embodiment of the claimed invention, as exemplary shown in FIG. 13, the ends of the barrier member (58) can have concave shapes (i.e., male ends), and the ends of the first, second and third barrier members (27, 47, 47a) can have protuberant shapes (i.e., female ends), such that these various ends interlock or mate when these components are coupled together as discussed herein to form the replaceable heating cartridge (100). It is appreciated that the shape of the ends can be reversed such that the male ends are at the first, second and third barrier members (27, 47, 47a) and the female ends are at the barrier members (58). That is, the ends of the first, second and third barrier members (27, 47, 47a) correspond to interlock or mate with the ends of the barrier members (58) to form the fluid path that wraps around the heater (50) multiple times. The fluid path provides a smooth passage for the fluid to flow therein from the first connection part (21) to the second connection part (22).

Figure 14:
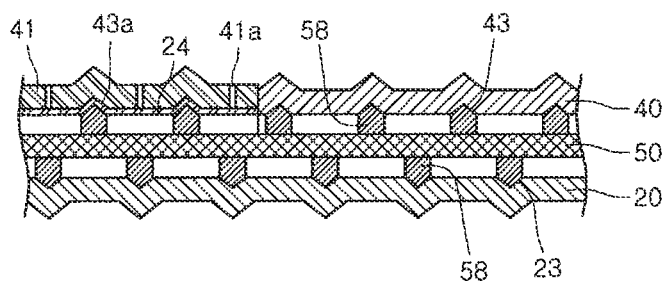
FIG. 14 is a view of a replaceable heating cartridge in accordance with an exemplary embodiment of the claimed invention.

In accordance with an exemplary embodiment of claimed invention, FIG. 14 shows a replaceable heating cartridge (100) in accordance with an exemplary embodiment of the claimed invention. The barrier members (58) are formed on the front and rear sides of the heater (50), as exemplary shown in FIG. 9, and holes or grooves (23, 43) are formed at the position corresponding to the barrier members (58) on the internal surfaces of the first and second cover members (20, 40). As noted herein, one of the first and second cover member (20 40) comprises a plurality of voids or openings (41a) to discharge air removed from the fluid by the filter (24). In accordance with an aspect of the claimed invention, the replaceable heating cartridge (100) of FIG. 14 can comprise an optional third cover member (41) comprising a plurality of holes and grooves (43a) formed thereon. As noted herein, the third cover member (41) can be formed integral with the second cover member (40), as exemplary shown in FIG. 11. The barrier members (58) formed on the heater (50) can be coupled to the heater (50) by an insert-injection, as discussed herein, and the holes (23, 43, 43a) of the first cover member (20), the second cover member (40) and the optional third cover member (41) can be formed when the first cover member (20), the second cover member (40) and the optional third cover member (41) are insert-injected.

In accordance with an exemplary embodiment of the claimed invention, the ends of the barrier (58) have protuberant shapes and are insertable into the holes (23, 43, 43a) of the first cover member (20), the second cover member (40) and the optional third cover (41), thereby interlocking with each other when these various components are coupled to form the replaceable heating cartridge (100), as discussed herein.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The invention claimed is:

1. A replaceable heating cartridge for warming a fluid, comprising:
   a heater having first and second sides;
   a first connecting portion to receive a fluid from an external source;
   a second connecting portion to supply a heated fluid;
   a plurality of barrier members disposed on each side of said heater;
   a pair of cover members, each cover member disposed on one side of said heater, configured to couple to each other with said heater and said barrier members therein between to form a body with a fluid path wrapping around said heater multiple times to warm said fluid flowing through said fluid path from said first connecting portion to supply said heated fluid at said second connecting portion; and
   an air filter disposed on said fluid path to remove air from said fluid.

2. The replaceable heating cartridge of claim 1, wherein said heater is a printed circuit board type (PCB-type) heater formed on an insulating substrate comprising resistive patterns formed on both surfaces of said insulating substrate.

3. The replaceable heating cartridge of claim 1, wherein said barrier members are formed on an internal surface of each cover member.

4. The replaceable heating cartridge of claim 3, wherein said each cover member and associated barrier members are formed by integral injection molding.

5. The replaceable heating cartridge of claim 3, wherein said barrier members on a first cover member are sloped in a first direction and said barrier members on a second cover member are sloped in a second direction to form said fluid path in a shape of a screw thread.

6. The replaceable heating cartridge of claim 1, wherein said air filter is disposed on an internal surface of one of said cover members.

7. The replaceable heating cartridge of claim 6, wherein said air filter is disposed towards the second connecting portion.

8. The replaceable heating cartridge of claim 6, wherein said air filter is disposed between said internal surface of said one of said cover members and said barrier members.

9. The replaceable heating cartridge of claim 6, wherein a portion of said one of said cover members in contact with said air filter comprises a plurality of openings to discharge from said fluid path air removed from said fluid by said air filter.

10. The replaceable heating cartridge of claim 9, further comprising a check valve in each of said plurality of openings to discharge air from said fluid path and to prevent entry of air into said fluid path from outside of said body of the replaceable heating cartridge.

11. The replaceable heating cartridge of claim 1, wherein said air filter is formed of a hydrophobic non-woven fabric to prevent passage of said fluid from said fluid path.

12. The replaceable heating cartridge of claim 2, wherein said PCB-type heater comprises at least one voltage electrode extending outside said body of the replaceable heating cartridge.

13. The replaceable heating cartridge of claim 12, wherein said at least one voltage electrode is configured to receive power from an external power source and to supply power to said resistive patterns of said PCB-type heater.

14. The replaceable heating cartridge of claim 13, wherein said resistive patterns on said first and second sides of said PCB-type heater are electrically divided.

15. The replaceable heating cartridge of claim 13 is installable in a housing configured to house the replaceable heating cartridge and connect to the said at least one voltage electrode and said at least one temperature sensing electrode.

16. The replaceable heating cartridge of claim 2, wherein said PCB-type heater comprises at least one temperature sensing electrode extending outside said body of the replaceable heating cartridge and at least one temperature sensor to measure the temperature of said fluid in said fluid path and connected to said at least one temperature sensing electrode.

17. The replaceable heating cartridge of claim 16 is installable in a housing configured to house the replaceable heating cartridge and connect to the said at least one temperature sensing electrode.

18. The replaceable heating cartridge of claim 1, wherein said barrier members are formed on said first and second sides of said heater.

19. The replaceable heating cartridge of claim 18, wherein said heater comprises a connecting hole to connect said barrier members formed on said first and second sides of said heater to each other.

20. The replaceable heating cartridge of claim 18, further comprising a coating material on both sides of said heater, said coating material having a melting point lower than a material of said barrier members such that said coating material dissolves when said barrier members are formed on said first and second sides of the heater, thereby integrating said heater with said barrier members.

21. The replaceable heating cartridge of claim 18, further comprising a plurality of holes on an internal surface of each cover member to receive ends of said barrier members formed on said first and second sides of said heater when said cover members are coupled to each other to form said body with said fluid path wrapping around said heater multiple times.

22. The replaceable heating cartridge of claim 3, further comprising second barrier members are formed on said first and second sides of said heater; and wherein ends of said barrier members formed on said internal surface of each cover member are shaped to mate or interlock with corresponding shaped ends of said second barrier members on said heater to form said fluid path wrapping around said fluid path multiple times.

* * * * *